US00PP13512P2

(12) United States Plant Patent
Carruth

(10) Patent No.: US PP13,512 P2
(45) Date of Patent: Jan. 28, 2003

(54) FLORIBUNDA ROSE PLANT NAMED 'WEKTORCENT'

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 09/995,072

(22) Filed: Nov. 27, 2001

(51) Int. Cl.[7] ..... A01H 5/00
(52) U.S. Cl. ..... Plt./143
(58) Field of Search ..... Plt./143, 142

*Primary Examiner*—Bruce R. Campell
*Assistant Examiner*—Susan B. McCormick
(74) *Attorney, Agent, or Firm*—Christie, Parker & Hale, LLP

(57) ABSTRACT

A new variety of Floribunda rose suitable for garden decoration, having flowers of orange and white striped coloration.

1 Drawing Sheet

BOTANICAL CLASSIFICATION

*Rosa hybrida.*

VARIETY DENOMINATION

'WEKTORCENT'.

BACKGROUND OF THE INVENTION

This invention relates to a new and distinct variety of Floribunda Rose. The varietal denomination of the new variety is 'WEKtorcent'. It has as its seed parent the variety known as 'WEKtorroc' (not patented) and as its pollen parent the variety known as 'WEKplapep' (U.S. Plant Pat. No. 10,126).

SUMMARY OF THE INVENTION

Among the features which distinguish the new variety from other presently available and commercial rose cultivars known to the inventor are the following combination of characteristics: its unusual orange and white striped flower coloration, its dark red new shoots, its numerous prickles and its very wide stipules with a red suffusion on the upper side. The plant has a rounded, bushy to somewhat spreading plant growth habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKtorcent' may be asexually propagated by cuttings, budding and grafting.

COMPARISON WITH PARENTS

The new variety may be distinguished from its seed parent, 'WEKtorroc' by the following combination of characteristics: whereas 'WEKtorroc' produces deep pink and cream striped more single petaled flowers (about 5 to about 8 petals), 'WEKtorcent' produces orange and white striped semi-double flowers with significantly higher petalage (about 11 to about 17 petals). The new variety is classified as a floribunda with a rounded, bushy to somewhat spreading growing habit, whereas 'WEKtorroc' is classified as a climber with significantly longer canes and a more spreading growing habit.

The new variety may be distinguished from its pollen parent, 'WEKplapep' by the following combination of characteristics: whereas 'WEKtorcent' produces orange and white striped semi-double flowers (about 11 to about 17 petals), 'WEKplapep' bears red and white striped double flowers with significantly higher petalage (about 31 to about 36 petals). The new variety has a mild apple-like frgrance whereas the pollen parent has a significantly stronger damask and spicy fragrance.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety usually bears its flowers singly, sometimes in clusters of two or more per stem. The clusters are irregular to somewhat rounded. Stems are strong and of short to medium length (about 32 to about 65 cm.). Outdoors, the plant blooms abundantly and nearly continuously during the growing season. The flowers have a mild apple-like fragrance.

BUD

The peduncle is about 3.8 to about 6.7 cm. in length, of average caliper (about 0.2 to about 0.4 cm. in diameter), and usually erect to somewhat stiff. It is moderately rough, with some stipitate glands and few small prickles. Peduncle color is between 144A and 147C often heavily suffused, especially on the side exposed to the sun, with between 183B and 187B.

Before the calyx breaks, the bud is about 1.2 to about 1.6 cm. in diameter at the widest point, about 1.4 to about 2.1 cm. in length, and pointed to moderately ovoid in shape with a somewhat conspicuous hypanthium. The surface of the bud bears some foliaceous appendages and numerous stipitate glands, usually with slender entire foliaceous parts extending beyond the tip of the bud about ¼ or more of its length. Bud color is between 144A and 147C often heavily suffused, especially on the side exposed to the sun, with between 183B and 187B.

The sepals are about 2.0 to about 2.7 cm. in length and about 0.7 to about 1.0 cm. in width at the widest point. The outer surface color of the sepal is between 144A and 147C often heavily suffused, especially on the side exposed to the sun, with between 183B and 187B. The inner surface color of the sepal is between 144B and 137B and covered with fine wooly tomentum; sepal margins are lined with numerous stipitate glands and hairs.

As the petals open (after the calyx breaks), the bud is about 1.8 to about 2.4 cm. in diameter at the widest point, about 2.3 to about 2.9 cm. in length, and ovoid to moderately pointed in form. The color of the under surfaces of the newly opened petals is irregularly striped and flecked with as dark as between 46A and 53A to as light as between 11D and 18C. The lighter colored portion of the petal that is exposed to the sun sometimes blushes to between 41D and 38A. At the point where the petal attaches, there is a moderately small zone of between 6C and 7C. The color of the upper surfaces of the newly opened petals is irregularly striped and flecked with as dark as between 45A and 53A to as light as between 40B and 33C. At the point where the petal attaches, there is a moderately small zone of between 7C and 12B. The pattern of coloration on the under side of the petal usually differs from the pattern of coloration on the upper petal side.

BLOOM

When fully open, the bloom ranges from about 8.2 to about 11.3 cm. in diameter. Petalage is semi-double with about 11 to 17 petals and about 2 to 5 petaloids irregularly arranged. When partially open, the bloom form is very cupped to slightly high centered, and the petals are moderately cupped to loosely spiraled with petal edges somewhat reflexed outward. When fully open, the bloom form is less cupped to somewhat flat, and the petals are somewhat cupped to slightly undulated wth petal edges more reflexed outward.

PETALS

The substance of the petals is moderately heavy and of medium to somewhat thick thickness, with upper surfaces moderately satiny and under surfaces moderately shiny. The outer petals are broadly rounded to somewhat obovate in shape with rounded apices. The inner petals are broadly obovate in shape with rounded apices, sometimes notched with one notch. The petals are about 3.7 to about 4.6 cm. in length and about 2.9 to about 4.7 cm. in width at the widest point. Petal margins are entire.

NEWLY OPENED FLOWER

The under surface color of the outer, intermediate and inner petals is irregularly striped and flecked with as dark as between 50A and 60A to as light as between 36C and 27C. The lighter colored portion of the petal sometimes blushes to near 49B. At the point where the petal attaches, there is a moderately small zone of between 6D and 5B.

The upper surface color of the outer, intermediate and inner petals is irregularly striped and flecked with as dark as between 40A and 47A to as light as between 27D and 155D. Sometimes on the edge of the outer most petals, the darker portion of the petals blush with between 53A and 59A. The lighter colored portion of the petals sometime blush to between 43D and 54B. At the point where the petal attaches, there is a moderately small zone of between 7C and 12B.

The pattern of coloration on the under side of the petal differs from the pattern of coloration on the upper petal side.

The general tonality of the newly opened flower is irregularly striped and flecked with as dark as between 40A and 47A to as light as between 27D and 155D. Sometimes on the edge of the outer most petals, the darker portion of the petals blush with between 53A and 59A. The lighter colored portion of the petals sometimes blush to between 43D and 54B.

THREE-DAY-OLD FLOWER

The under surface color of the outlet and inner petals is irregularly striped and flecked with as dark as between 50A and 60B to as light as between 49D and 155D. The lighter colored portion of the petal sometimes blushes to near 48C. At the point where the petal attaches, there is a moderately small zone of between 8D and 4D.

The upper surface color of the outer and inner petals is irregularly striped and flecked with as dark as between 43C and 53B to as light as between 49D and 155D. Sometimes, the darker portion of the petals blush to as dark as between 58A and 59B. The lighter colored portion of the petals sometime blush to between 43C and 58A. At the point where the petal attaches, there is a moderately small zone of between 10D and 12D.

The pattern of coloration on the under side of the petal differs from the pattern of coloration on the upper petal side.

The general tonality of the three-day-old flower is irregularly striped and flecked with as dark as between 43C and 53B to as light as between 49D and 155D. Sometimes, the darker portion of the petals blush to as dark as between 58A and 59B. The lighter colored portion of the petals sometime blush to between 43C and 58A.

On the spent bloom, the petals usually drop off cleanly.

In October in Upland, Calif., blooms on the bush growing outdoors generally last about four to five or more days. Cut roses from plants grown outdoors and kept at normal indoor living temperatures generally last about four to five or more days.

MALE REPRODUCTIVE ORGANS

Stamens are many in number (average about 99) and are arranged regularly about the pistils; a few are mixed with petaloids. The filaments are of average to somewhat long length (about 0.5 to about 1.2 cm.), most with anthers. Filaments are between 12B and 9B in color. The anthers are somewhat small for the class and all open approximately at the same time. Anther color is between 23B and 24B when immature and between 163A and 200B at maturity. Pollen is abundant.

FEMALE REPRODUCTIVE ORGANS

Pistils vary in number (average about 68). The styles are moderately even, moderately short in length (about 0.3 to about 0.6 cm.), average in caliper, and loosely bunched. Stigma color is between 20A and 16A. Style color is between 2D and 1D often heavily suffused near the top with near 53A. Ovaries are ususally all enclosed in the calyx, although few may protrude from the calyx.

Hips are of somewhat short to average (about 1.3 to about 1.9 cm.), globular to somewhat ovoid in form, and between 25B and 28B in color when ripe. The hip surface is smooth with few stipitate glands and thick fleshy walls. The sepals are moderately permanent. The seeds are irregularly rounded, smooth in texture, approximately 12 to about 20 per hip, about 0.3 to about 0.6 cm. in diameter at the widest point and between 164C and 161A in color.

FOLIAGE

The compound leaves are usually comprised of three to five or more leaflets and are borne abundantly. The five-leaflet leaves are about 9.1 to about 12.3 cm. in length and about 7.6 to about 9.9 cm. in width at the widest point, moderately heavy to somewhat crisp in texture, and somewhat semi-glossy in finish. The terminal leaflets are about 4.3 to about 6.2 cm. in length and about 2.7 to about 4.0 cm. in width at the widest point, shaped moderately oval to somewhat broadly obovate with moderately mucronate to somewhat acute apices and round to slightly acute bases. Their margins are usually simply serrate.

The upper surface color of the mature leaf is between 147A and 139A. The under surface color of the mature leaf is between 146B and 138C. The upper surface color of the young leaf is near 146B, usually heavily suffused with between 187A and 187B. The under surface color of the young leaf is near 146B, usually heavily suffused with between 187A and 187B.

The rachis is somewhat light in caliper and somewhat rough. The upper side is shallowly grooved with few hairs and numerous stipitate glands on the edges of the grooves. The under side of the rachis is somewhat rough with few hairs, numerous stipitate glands and very few small prickles. The rachis color is between 144A and 146C.

The stipules are about 1.6 to about 2.2 cm. in length and very wide (about 0.6 to about 0.9 cm.) with very long straight points that usually turn out at an angle of more than 45 degrees. The stipules color is between 147B and 144B sometimes lightly suffused on the upper side with between 187B and 187C.

The petiole is about 0.8 to about 1.7 cm. in length and about 0.1 to about 0.2 cm in diameter at the widest point. The petiole color is between 147B and 144A sometimes lightly suffused with between 187B and 187C.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has a rounded, busy to somewhat spreading medium height growth habit (about 123 to about 141 cm. in height and about 123 to about 141 cm. spread at the widest point), with very full branching. It displays moderately vigorous growth and the canes are of somewhat heavy caliper for the class.

The color of the major stems is between 146C and 144A. They bear many large prickles that are about 0.6 to about 0.9 cm. in length. The large prickles are almost straight and angled slightly downward with a medium length somewhat narrow oval base; prickle color is between 164A and 165B. The major stem bears several small prickles of similar shape and coloration.

The color of the branches is between 144A and 138A. They bear some large prickles which are of similar size and shape to the large prickles on the major stems; prickle color is between 166D and 165C. The branches bear numerous small prickles of similar shape and coloration.

The color of the new shoots is between 144B and 138B often heavily suffused with between 187C and 187B. They bear numerous large prickles which are of similar size and shape to the large prickles on the major stems; prickle color is between 144A and 144B usually heavily suffused with between 187C and 187B. The shoots bear numerous small prickles of similar shape and coloration.

I claim:

1. A new and distinct Floribunda rose plant of the variety substantially as described and illustrated herein.

* * * * *

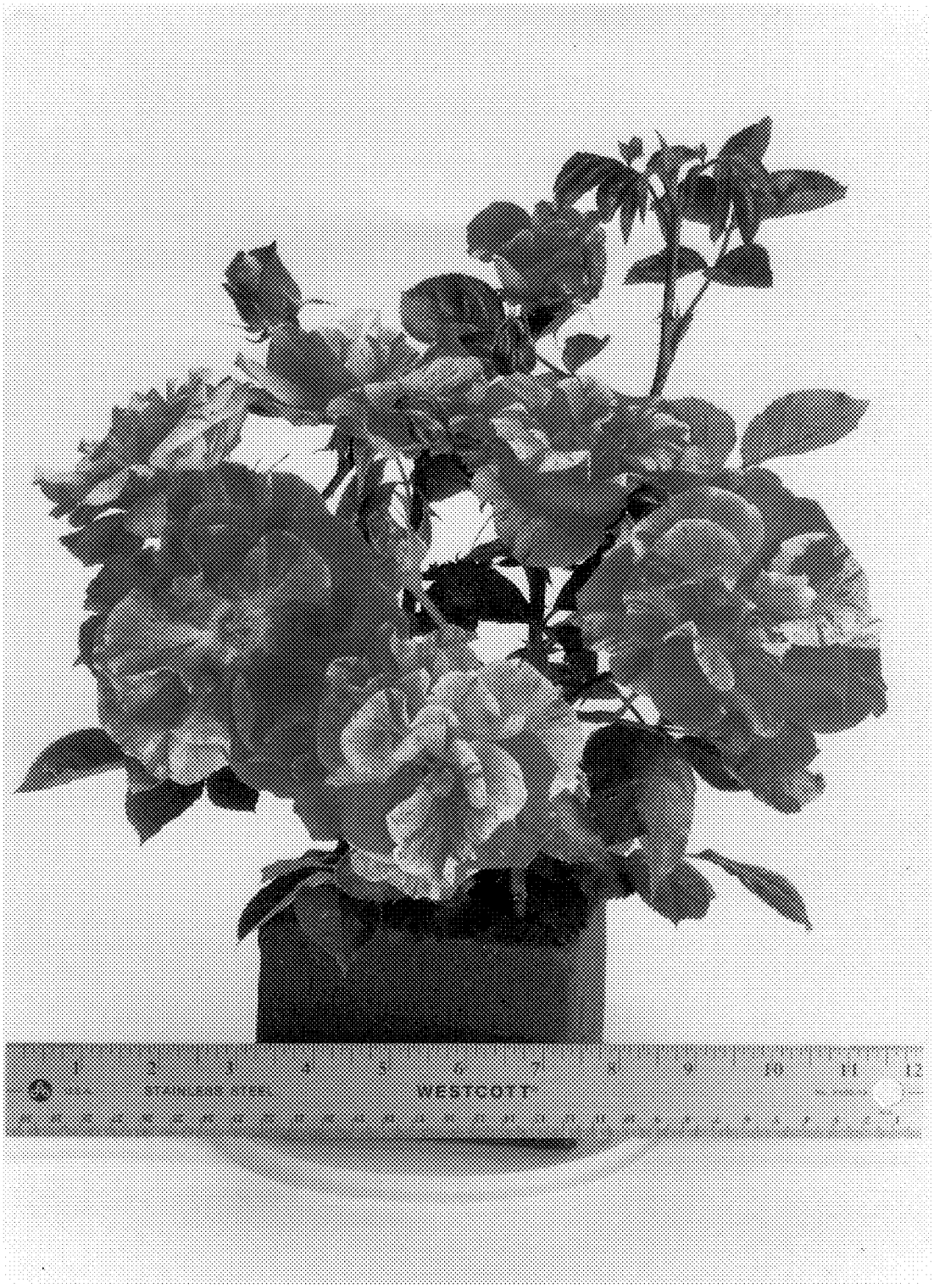
WESTCOTT